(12) United States Patent
Shoshtaev

(10) Patent No.: US 10,667,852 B2
(45) Date of Patent: Jun. 2, 2020

(54) LAMINAR FIXATION CLAMP AND METHOD

(71) Applicant: Life Spine, Inc., Huntley, IL (US)

(72) Inventor: Eugene Shoshtaev, Del Mar, CA (US)

(73) Assignee: Life Spine, Inc., Huntley, IL (US)

( * ) Notice: Subject to any disclaimer, the term of this patent is extended or adjusted under 35 U.S.C. 154(b) by 0 days.

(21) Appl. No.: 15/948,817

(22) Filed: Apr. 9, 2018

(65) Prior Publication Data

US 2018/0289403 A1 Oct. 11, 2018

Related U.S. Application Data

(60) Provisional application No. 62/483,731, filed on Apr. 10, 2017.

(51) Int. Cl.
*A61B 17/84* (2006.01)
*A61B 17/70* (2006.01)
*A61B 17/64* (2006.01)
*A61B 17/00* (2006.01)

(52) U.S. Cl.
CPC ........ *A61B 17/842* (2013.01); *A61B 17/6466* (2013.01); *A61B 17/7041* (2013.01); *A61B 17/7049* (2013.01); *A61B 17/7053* (2013.01); *A61B 2017/00367* (2013.01)

(58) Field of Classification Search
CPC ............ A61B 17/7047; A61B 17/7053; A61B 17/842
USPC ........................................................ 606/263
See application file for complete search history.

(56) References Cited

U.S. PATENT DOCUMENTS

| 5,961,517 | A | 10/1999 | Biedermann et al. |
|---|---|---|---|
| 8,066,739 | B2 | 11/2011 | Jackson |
| 8,728,083 | B2 | 5/2014 | Baccelli et al. |
| 9,173,685 | B2 | 11/2015 | Lindquist et al. |
| 9,757,167 | B2 | 9/2017 | Hsu et al. |
| 10,022,159 | B2 | 7/2018 | Simpson |
| 10,307,186 | B2 | 6/2019 | Schafer et al. |

(Continued)

FOREIGN PATENT DOCUMENTS

| EP | 2047813 A1 | 4/2009 |
|---|---|---|
| EP | 2 777 569 A1 | 9/2014 |
| WO | WO-2016/145042 A1 | 9/2016 |

OTHER PUBLICATIONS

International Search Report and Written Opinion for International Application No. PCT/US2018/026747, dated Jul. 23, 2018, 11 pages.

(Continued)

*Primary Examiner* — Nicholas J Plionis
(74) *Attorney, Agent, or Firm* — Foley & Lardner LLP

(57) ABSTRACT

A laminar fixation clamp has a body that utilizes a clam-shell style pivot controlled by a set screw, to grasp and attach to a spine rod, while receiving a laminar fixation band that can loop around a lamina of a vertebra in order to hold the laminar fixation clamp onto the vertebra. One form comprises a two-piece structure while another form comprises a single-piece structure. In each case, an upper and lower clamping structure situated at a front of the laminar fixation clamp, is received over and onto the spine rod, while a laminar fixation band is received through clamp. The set screw controls the amount of pivoting and thus the clamping force exerted onto the spine rod.

17 Claims, 3 Drawing Sheets

(56) References Cited

U.S. PATENT DOCUMENTS

| | | | |
|---|---|---|---|
| 2005/0131404 A1* | 6/2005 | Mazda | A61B 17/7035 606/264 |
| 2005/0192570 A1 | 9/2005 | Jackson | |
| 2005/0228375 A1* | 10/2005 | Mazda | A61B 17/7041 606/263 |
| 2006/0069391 A1 | 3/2006 | Jackson | |
| 2009/0138048 A1 | 5/2009 | Baccelli et al. | |
| 2011/0106185 A1 | 5/2011 | Gil et al. | |
| 2011/0112581 A1 | 5/2011 | Clement | |
| 2012/0022592 A1* | 1/2012 | Belliard | A61B 17/7053 606/263 |
| 2012/0271354 A1* | 10/2012 | Baccelli | A61B 17/7053 606/263 |
| 2013/0268011 A1 | 10/2013 | Rezach et al. | |
| 2014/0094850 A1 | 4/2014 | Clement et al. | |
| 2014/0257397 A1 | 9/2014 | Akbarnia et al. | |
| 2014/0257401 A1* | 9/2014 | George | A61B 17/7041 606/278 |
| 2016/0157896 A1 | 6/2016 | Palmer et al. | |
| 2016/0242825 A1 | 8/2016 | Simpson et al. | |
| 2016/0262806 A1 | 9/2016 | Hsu et al. | |
| 2019/0183553 A1 | 6/2019 | Bosshard et al. | |

OTHER PUBLICATIONS

International Search Report and Written Opinion for International Application No. PCT/US2018/026982, dated Jul. 24, 2018, 14 pages.

International Preliminary Report on Patentability on PCT/US2018/026747 dated Oct. 24, 2019, 12 pages.

International Preliminary Report on Patentability on PCT/US2018/026883 dated Oct. 24, 2019, 8 pages.

International Preliminary Report on Patentability on PCT PCT/US2018/026982 dated Oct. 24, 2019, 12 pages.

Search Report for International Application No. PCT/US2018/026883, dated Jul. 24, 2018, 12 pages.

* cited by examiner

LAMINAR FIXATION CLAMP AND METHOD

CROSS-REFERENCE TO RELATED APPLICATIONS

This U.S. non-provisional patent application claims the benefit of and/or priority under 35 U.S.C. § 119(e) to U.S. provisional patent application Ser. No. 62/483,731 filed Apr. 10, 2017 titled "Laminar Fixation Clamp and Method," the entire contents of which is specifically incorporated herein by reference.

FIELD OF THE INVENTION

The present invention relates to systems, implants and methods for orthopedic fixation of the spine and, more particularly, to systems, implants and methods for retaining a spine rod relative to a vertebra of the spine.

BACKGROUND OF THE INVENTION

Spine issues such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spine disorders typically result in symptoms including deformity, pain, nerve damage, and partial or complete loss of mobility. Non-surgical treatments, such as medication, rehabilitation and exercise can be effective, however, may fail to relieve the symptoms associated with these disorders. In some cases, non-surgical treatment is not an option. If non-surgical treatment fails or is not available, surgical treatment is required.

Surgical treatment of the aforementioned spine disorders includes correction, fusion, fixation, discectomy, laminectomy, and implants. Correction treatments used for positioning, alignment and stabilization of the spine employ implants such as spine (vertebral) rods and vertebral bone screw assemblies that provide connection to the spine rod, as well as other implants. Because of complex anatomies, severe spinal deformities, compromised pedicle anatomy, and/or poor vertebral bone quality, vertebral bone screw assemblies cannot be used. In these cases a laminar band and associated implant (a laminar fixation implant) is used to connect the spine rod to a vertebra, wherein the implant attaches to the spine rod and the band is received around the lamina or sub-lamina of the vertebra utilizing the strength of the laminar cortical bone. Most laminar fixation implants are installed using an installation tool specifically designed for the particular laminar fixation implant, creating a laminar fixation system.

While there are many styles of laminar fixation implants and laminar fixation systems, most are generally awkward, cumbersome and/or difficult to effectively use. There is therefore a need for a more efficient laminar fixation implant and/or laminar fixation system.

SUMMARY OF THE INVENTION

A laminar fixation clamp has a body that utilizes a clam-shell style pivot controlled by a set screw, to grasp and attach to a spine rod, while receiving a laminar fixation band that can loop around a lamina of a vertebra in order to hold the laminar fixation clamp onto the vertebra.

One form of the present laminar fixation clamp comprises a two-piece structure along with the set screw.

Another form of the present laminar fixation clamp comprises a single-piece structure along with the set screw.

In all cases, an upper and lower clamping structure situated at a front of the laminar fixation clamp, is received over and onto the spine rod, while a laminar fixation band is received through clamp. The set screw controls the amount of pivoting and thus the clamping force exerted onto the spine rod.

The laminar fixation clamp, along with a laminar fixation band comprises a laminar fixation system or implant.

Further aspects of the present invention will become apparent from consideration of the figures and the following description of the invention. A person skilled in the art will realize that other forms of the invention are possible and that the details of the invention can be modified in a number of respects without departing from the inventive concept. The following figures and description are to be regarded as illustrative in nature and not restrictive.

BRIEF DESCRIPTION OF THE DRAWINGS

The features of the invention will be better understood by reference to the accompanying drawings which illustrate forms of the present invention, wherein.

It should be appreciated that dimensions of the components, structures, and features of the present laminar fixation clamp can be altered as desired.

DETAILED DESCRIPTION OF THE INVENTION

Referring to FIGS. 1-4, there is shown a laminar fixation clamp, generally designated 10, fashioned in accordance with the present principles. The laminar fixation clamp 10 is configured to attach onto a spine rod R (see FIG. 4) and be held to the lamina, sub-lamina, or other part of a vertebra (not shown) via a laminar band 50 (see FIG. 4) by a laminar band loop 51 (see FIG. 4) that wraps around the lamina, sub-lamina, or other part of a vertebra.

Figure 1:
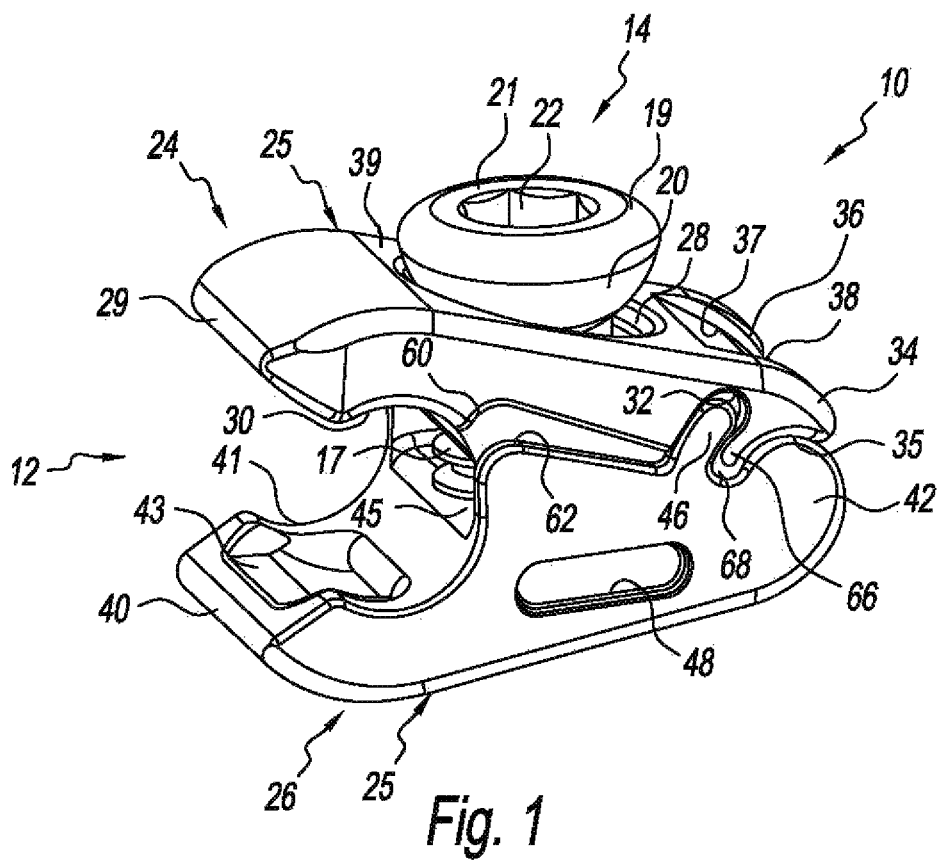
FIG. 1 is an isometric view of a two-piece form of a laminar fixation clamp fashioned in accordance with the present principles, the two-piece laminar fixation clamp shown in an open or pre-installation position.
Figure 2:
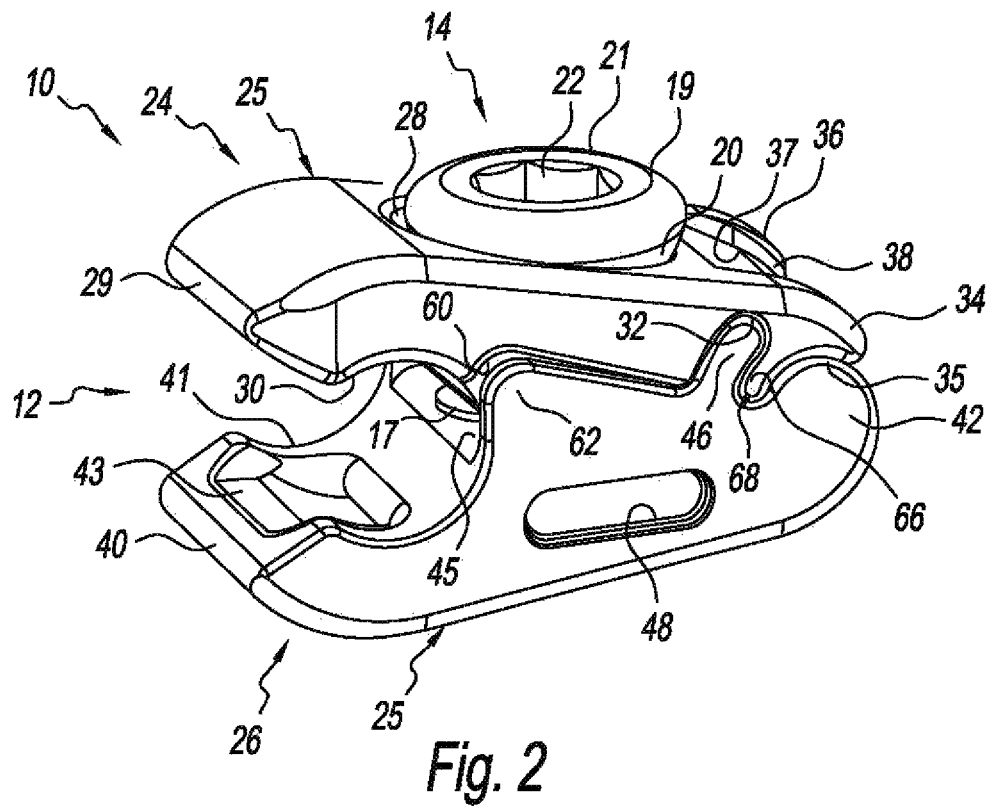
FIG. 2 is an isometric view of the two-piece laminar fixation clamp of FIG. 1 shown in a closed or post-installation position.
Figure 3:
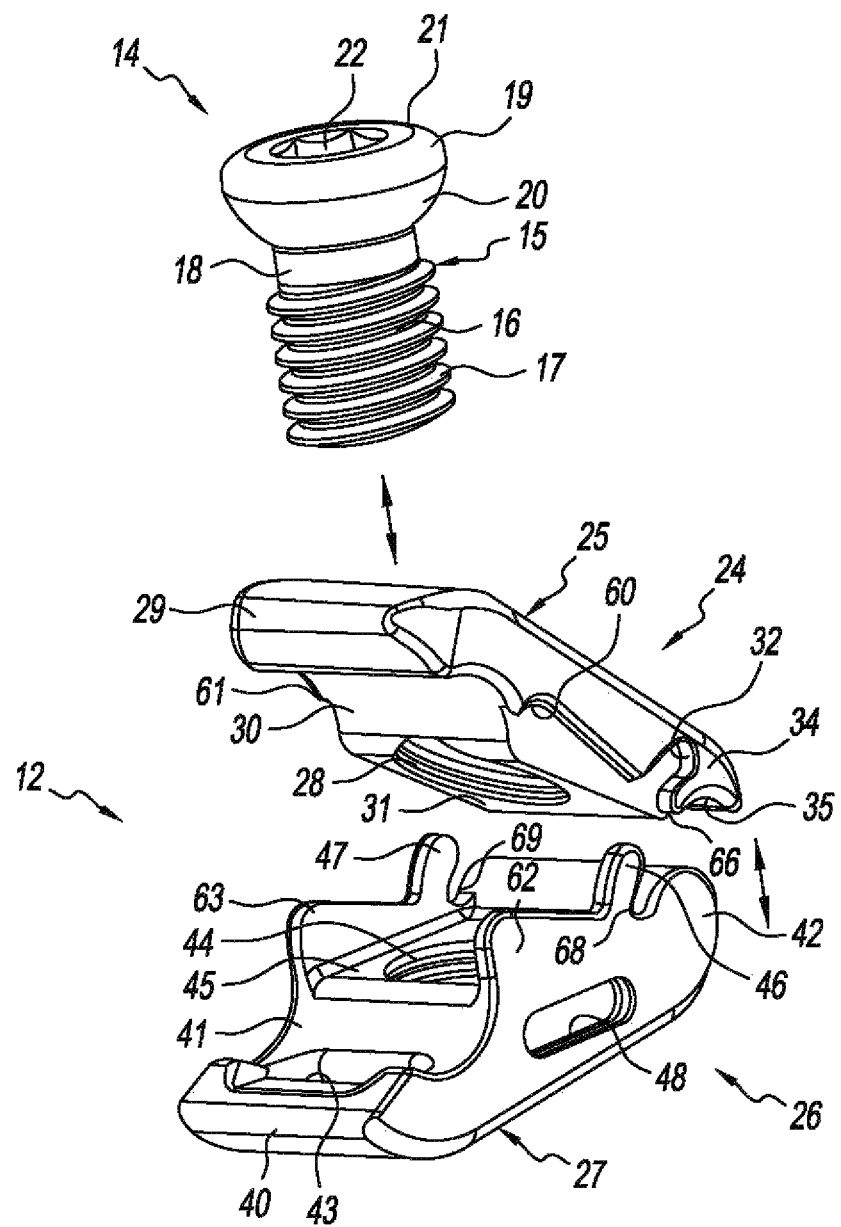
FIG. 3 is an exploded view of the laminar fixation clamp of FIG. 1.
Figure 4:
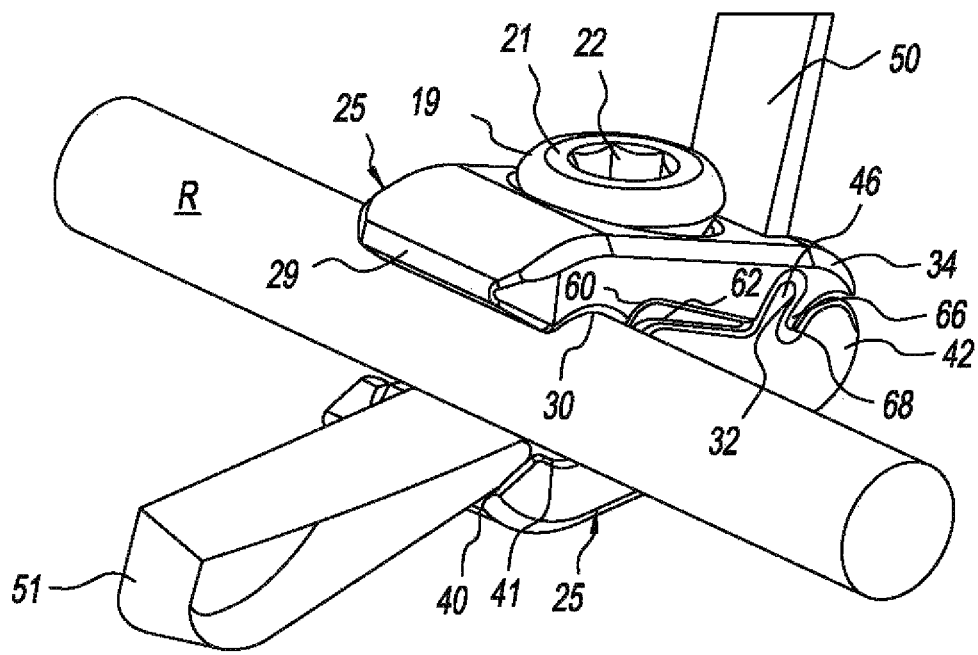
FIG. 4 is an isometric view of the laminar fixation clamp of FIG. 1 attached to a spine rod along with a laminar fixation band received in the laminar fixation clamp and forming a loop that would be placed around the lamina or sub-lamina of a vertebra.

The laminar fixation clamp 10 is characterized by a body 12 preferably, but not necessarily, formed of PEEK, other plastic or polymer, titanium, stainless steel, an alloy thereof, ceramic, or other bio-compatible material having appropriate characteristics for its intended purpose as described herein, and a set screw 14. The body has a two-piece construction consisting of a first component 24 and a second component 26 that are configured to "clamshell" pivot with respect to each other. FIG. 4 provides the first and second components 24, 26 in an exploded view that shows how the first and second components 24, 26 join. The set screw 14 controls pivoting of the first and second components 24, 26 as described more fully below in order to close the first and second components 24, 26 such that the first and second components 24, 26 clamp onto a spine rod. The set screw 14 also allows pivoting of the first and second components 24, 26 in order to open the first and second components 24, 26 and release the spine rod if desired.

The set screw 14 is characterized by body 15 having a head 19, a neck 18 extending from one side of the head 19, a shaft 16 extending axially from the neck 18, and external thread/threading 17 on the shaft 16. The shaft 17 has a blunt or flat end opposite the head 19 such that the set screw 14 is similar to a machine screw. The threading 17 of the shaft 16 are configured to engage threads/threading of the first component 24 and of the second component 26. The head 19 has a socket 22 in its upper surface 21 that is configured to receive a like configured installation tool (not shown). The socket 22 may be configured as a hexalobe, hexagon, or other shape, the installation tool therefore having a like shaped configuration. The head 19 has an inwardly angled portion 20 that tapers to the neck 18. The set screw 14 is formed of a suitable biocompatible material such as, but not limited to, titanium, stainless steel, an alloy of either, as well as polymers, plastics, ceramics, or the like.

The first component 24 is characterized by a generally elongated body 25 defining a generally planar upper side 39 and a generally planar lower side 31, the nomenclature upper and lower being arbitrary, with a nose 29 at one end of the body 25, and a rear/rear notch 38 at the other end of the body 25. An internally threaded bore 28 extends through the body 25 from the upper side 39 to the lower side 31 and is sized and configured to receive the threaded shaft 16 of the set screw 14 but not allow the head 19 to extend there-through by seating the head 19 into an upper area of the bore 28 (see, e.g. FIG. 2).

The underside 30 of the nose 29 has a curved surface in like manner and configuration as the outside surface of a spine rod in order to grasp a portion of the spine rod (see, e.g., FIG. 4). A first lateral flange 34 is formed at the end opposite the nose 29 and at a lateral side of the body 25, while a second lateral flange 36 is formed at the end opposite the nose 29 and a lateral side of the body 25 opposite the first lateral flange 34. The rear/rear notch 38 is defined between the first lateral flange 34 and the second flange 36. The rear notch 38 allows the laminar band B to extend therethrough (see FIG. 4). An underside 35 of the first lateral flange 34 is curved to provide a pivot area. An underside (not seen) of the second lateral flange 36 is likewise curved to provide a pivot area. The two pivot areas (undersides) cooperate with an elongated curved seat or boss 42 of the second component 26.

A first lateral lobe 66 and a first lateral pocket 32 are defined in the underside of the first lateral flange 34. A second lateral lobe (not seen) and a second lateral pocket (not seen) are likewise defined in the underside of the second lateral flange 36. These structures provide positive coupling of the first and second components 24, 26 and as additional pivot seats. The underside of the body 25 proximate the rod reception area 30 further includes a first lateral cusp 60 and a second lateral cusp 61 that cooperate with structures of the second component to provide a position coupling of the first and second components 24, 26.

The second component 26 is characterized by a generally elongated body 27 defining a generally planar upper shelf or side 45 and a generally planar lower side (not seen), the nomenclature upper and lower being arbitrary, with a nose 40 at one end of the body 27, and the elongated curved seat or boss 42 at a rear of the body 27 opposite the nose 40. An internally threaded bore 44 extends through the body 27 from the upper side 45 to the lower side (not seen) and is sized and configured to receive the threaded shaft 16 of the set screw 14.

The upper side 41 of the nose 40 has a curved surface in like manner and configuration as the outside surface of a spine rod in order to grasp a portion of the spine rod (see, e.g., FIG. 4). A first front lateral boss 62 and a second front lateral boss 63 are formed proximate the rod reception area 41 that are configured to receive and/or mate respectively with the first lateral cusp 60 and the second lateral cusp 61 of the first component 24 (see, e.g., FIG. 2). A first lateral ear 46 and a first lateral notch 68 are defined proximate the pivot surface 42 on a first lateral side of the second component 26. A second lateral ear 47 and a second lateral notch 69 are defined in the underside of the second lateral flange 36 are defined proximate the pivot surface 42 on a second lateral side of the second component 26 opposite the first lateral side. These structures mate with the first lateral lobe 66 and the first lateral pocket 32, and the second lateral lobe (not seen) and the second lateral pocket (not seen) to provide positive coupling of the first and second components 24, 26.

The body 27 further includes an opening 48 in one side of the body 27 and a second opening (not seen) in the other side of the body 27 opposite the opening 48. The openings allow receipt of an installation tool, and other applications/use. Further, the body 27 has a channel 43 that extends from the nose 40, through the body, and out the rear for the laminar band.

As discerned from the figures, the laminar fixation clamp 10 is pivotally controlled by the set screw 14. One direction of rotation brings the first and second components 24, 26 together by the rear pivot of the two components 24, 26, while the other direction of rotation spreads the first and second components apart 24, 26. Closing of the first and second components 24, 26 brings the respective noses 29, 40 and their rod retention area 30, 41 onto the spinal rod R. The laminar band can be threaded through the channel 43 to form a loop 51, the free end of which (see FIG. 4) is clamped at the rear pivot of the first and second components between the pivot boss 42 of the second component 26 and the pivot structures of the first component 24.

Figure 5:
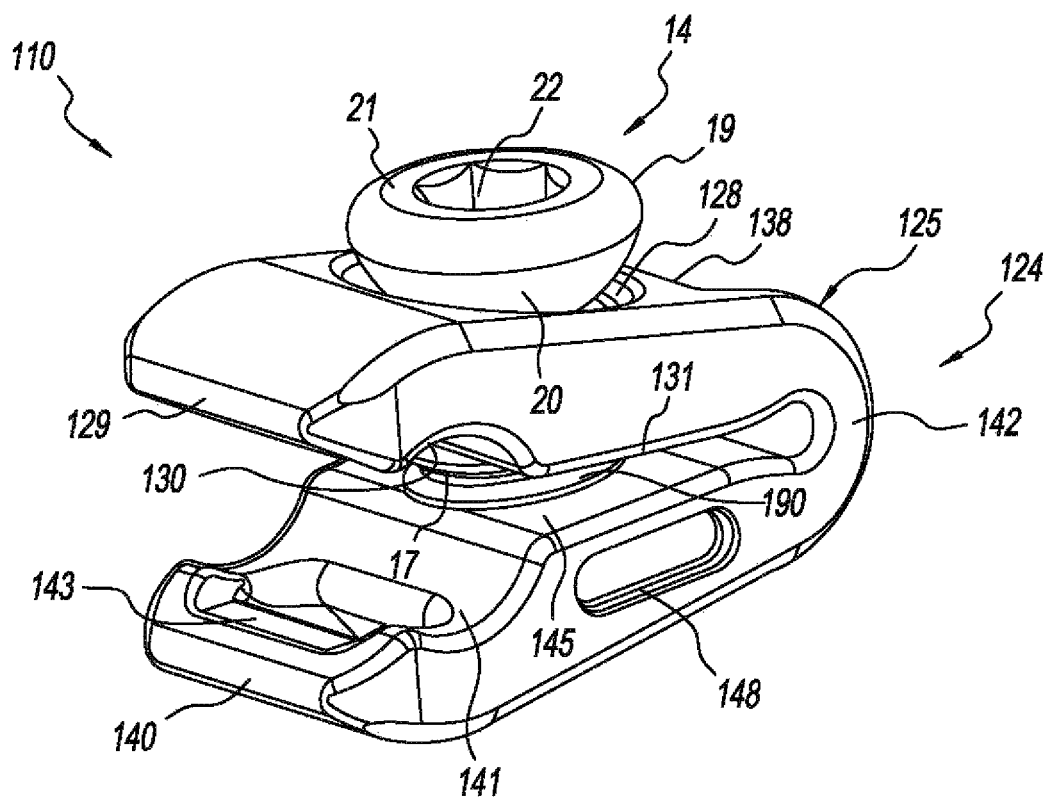
FIG. 5 is an isometric view of a one-piece form of a laminar fixation clamp fashioned in accordance with the present principles, the two-piece laminar fixation clamp shown in an open or pre-installation position.

Referring to FIG. 5, there is shown another laminar fixation clamp, generally designated 110, fashioned in accordance with the present principles. The laminar fixation clamp 110 is configured to attach onto the spine rod R and be held to the lamina, sub-lamina, or other part of a vertebra (not shown) via a laminar band 50 by a laminar band loop 51 that wraps around the lamina, sub-lamina, or other part of a vertebra in the same and/or similar fashion as the laminar fixation clamp 10.

The laminar fixation clamp 110 is characterized by a one-piece clamp 124 defined by a body 125 that is preferably, but not necessarily, formed of PEEK, other plastic or polymer, titanium, stainless steel, an alloy thereof, ceramic, or other bio-compatible material having appropriate characteristics for its intended purpose as described herein, and the set screw 14. The body 125 is of a one-piece construction having similar features to the laminar fixation clamp 10 such that the body 125 is configured to "clamshell" pivot via the set screw 14 in like manner to the laminar fixation clamp 10.

The one-piece body 125 is "folded" relative to itself thereby defining an elastic pivot 142 at a rear of the body 125. A notch 138 is provided in the rear of the body 125 that allows the laminar band B to extend therethrough. An internally threaded bore 128 for receipt of the set screw 14 is provided in the upper portion of the body 125, while a threaded bore 190 is provided in the lower portion of the body 125. The set screw 14 brings the upper and lower portions together through bending of the body at the rear 142 thereof to clasp a spine rod. In this regard, an underside 130 of an upper nose 129 of the upper portion of the body 125 is curved in like manner as a spine rod, while an upperside 141 of the of a lower nose 140 of the lower portion of the body 125 is likewise curved in like manner as a spine rod. The body 125 further includes an opening 148 in one side of the body 125 and a second opening (not seen) in the other side of the body 125 opposite the opening 148. The openings allow receipt of an installation tool, and other applications/use. Further, the body 125 has a channel 143 that extends from the nose 140, through the body, and out the rear 138 for the laminar band.

A method of installation includes threading a laminar band through the laminar fixation clamp 10, 110, clamping the laminar fixation clamp onto a spine rod, looping the laminar band around a lamina, sub-lamina or other vertebral bone/bone portion, then tightening the laminar band accordingly.

What is claimed is:

1. A laminar fixation implant comprising:
a set screw having a head and an externally threaded shank extending from the head; and
a laminar fixation band having a first portion, a second portion, and an intermediate portion, and
a body comprising:
a first component and a second component separate from the first component, the first component and the second component each comprising a rear portion and a front portion, the first component pivotally coupled to the second component at the rear portions thereof,
a channel in the lower portion extending from the front portion of the lower portion to the rear portion of the second component, the channel is configured to receive the laminar fixation band wherein the intermediate portion of the laminar fixation band extends from the channel proximate the front portion of the second component,
an upper spine rod reception area on an underside of the first component proximate the front portion of the first component,
a lower spine rod reception area on an upperside of the second component proximate the front portion of the second component,
an upper threaded bore in the first component for receipt of the set screw,
a lower threaded bore in the second component for receipt of the set screw,
wherein the first component comprises first and second lateral lobes,
wherein the second component comprises first and second lateral notches;
wherein rotation of the set screw causes the first and second portions to pivot and compress relative to each other between a first position and a second position;
wherein in the first position the first and second lateral notches partially receive the first and second lateral lobes;
wherein in the second position the first and second lateral notches further receive the first and second lateral lobes and the first and second spine rod reception areas to grasp onto a spine rod.

2. The laminar fixation implant of claim 1, wherein the first component comprises first and second lateral pockets;
wherein the second component comprises first and second lateral ears;
wherein in the first position the first and second lateral pockets partially receive the first and second lateral ears;
wherein in the second position the first and second lateral pockets further receive the first and second lateral ears.

3. The laminar fixation implant of claim 2, wherein the upper threaded bore is disposed in the middle of the first component, and the lower threaded bore is disposed in the middle of the second component.

4. The laminar fixation implant of claim 1, wherein the upper threaded bore is disposed in the middle of the first component, and the lower threaded bore is disposed in the middle of the second component.

5. The laminar fixation implant of claim 1, wherein the implant is formed of a bio-compatible metal.

6. The laminar fixation system of claim 1, wherein the first component comprises first and second lateral cusps and the second component comprises first and second lateral bosses;
wherein in the second position the first and second lateral cusps receive the first and second lateral bosses.

7. A laminar fixation system comprising:
a set screw having a head and an externally threaded shank extending from the head;
a laminar fixation band having a first portion, a second portion, and an intermediate portion; and
a body comprising:
a first component and a second component separate from the first component, each component comprising a rear portion and a front portion, the first component pivotally coupled to the second component at the rear portions thereof, the first component comprising a curved underside proximate its rear portion, the second component comprising a curved seat proximate its rear portion and configured to slidably engage the curved underside of the first component,
a channel in the second component extending from the front portion of the second component to the rear portion of the second component, the channel is configured to receive the laminar fixation band, wherein the intermediate portion of the laminar fixation band extends from the channel the first and second portions of the laminar fixation band is clamped proximate the front portion of the second component,
an upper spine rod reception area on the first component proximate the front portion of the first component,
a lower spine rod reception area on an upperside of the second component proximate the front portion of the second component,
an upper threaded bore in the first component for receipt of the set screw,
a lower threaded bore in the second component for receipt of the set screw;
wherein rotation of the set screw causes the first component and the second component to pivot relative to each other between a first position and a second position, wherein in the second position the first and second spine rod reception areas grasp onto a spine rod and the first and second portions of the laminar fixation band are clamped between the curved underside of the first component and the curved seat of the second component.

8. The laminar fixation system of claim 7, wherein the first component comprises first and second lateral pockets and first and second lateral lobes,
   wherein the second component comprises first and second lateral ears and first and second lateral notches,
   wherein in the second position the first and second lateral pockets receive the first and second lateral ears, and the first and second lateral notches receive the first and second lateral lobes.

9. The laminar fixation system of claim 7, wherein the upper threaded bore is disposed in the middle of the first component, and the lower threaded bore is disposed in the middle of the second component.

10. The laminar fixation system of claim 7, wherein the first component comprises first and second lateral cusps and the second component comprises first and second lateral bosses; wherein in the second position the first and second lateral cusps receive the first and second lateral bosses.

11. The laminar fixation system of claim 7, wherein the upper threaded bore is disposed in the middle of the first component, wherein the lower threaded bore is disposed in the middle of the second component, and wherein the second component comprises first and second lateral openings configured to receive an installation tool.

12. The laminar fixation system of claim 7, wherein the implant is formed of a bio-compatible metal.

13. A method of retaining a spine rod relative to a vertebra, the method comprising:
   providing a laminar fixation band having a first portion, a second portion, and an intermediate portion;
   providing a laminar fixation implant having:
      a set screw having a head and an externally threaded shank extending from the head; and
      a body comprising:
         a first component and a second component separate from the first component, the first component and the second component each comprising a rear portion and a front portion, the upper portion pivotally coupled to the lower portion at the rear portions thereof,
         a channel in the lower portion extending from the front portion of the lower portion to the rear portion of the second component, the channel is configured to receive the laminar fixation band wherein the intermediate portion of the laminar fixation band extends from the channel proximate the front portion of the second component,
      an upper spine rod reception area on an underside of the first component,
      a lower spine rod reception area on an upperside of the second component proximate the front portion of the second component,
      an upper threaded bore in the first component for receipt of the set screw,
      a lower threaded bore in the second component for receipt of the set screw;
      wherein the first component comprises first and second lateral pockets,
      wherein the second component comprises first and second lateral ears;
      wherein rotation of the set screw causes the first and second portions to pivot and compress relative to each other between a first position and a second position, wherein in the first position the first and second lateral pockets partially receive the first and second lateral ears, wherein in the second position the first and second lateral pockets further receive the first and second lateral ears and the first and second spine rod reception areas to grasp onto a spine rod;
   clamping the laminar fixation implant onto the spine rod;
   threading the laminar fixation band through the laminar fixation implant;
   looping the laminar fixation band around a lamina of a vertebra; and
   tightening the laminar fixation band around the lamina.

14. The method of claim 13, wherein:
   the first component comprises first and second lateral lobes; and
   the second component comprises first and second lateral notches;
   in the first position the first and second lateral notches partially receive the first and second lateral lobes and
   in the second position the first and second lateral notches further receive the first and second lateral lobes.

15. The method of claim 14, wherein the upper threaded bore is disposed in the middle of the first component, and the lower threaded bore is disposed in the middle of the second component.

16. The method of claim 13, wherein the upper threaded bore is disposed in the middle of the first component, and the lower threaded bore is disposed in the middle of the second component.

17. The method of claim 13, wherein the implant is formed of a bio-compatible metal.

* * * * *